US008716015B2

(12) United States Patent
Pollack et al.

(10) Patent No.: US 8,716,015 B2
(45) Date of Patent: May 6, 2014

(54) MANIPULATION OF CELLS ON A DROPLET ACTUATOR

(75) Inventors: Michael G. Pollack, Durham, NC (US); Vamsee K. Pamula, Durham, NC (US); Allen E. Eckhardt, Durham, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 1069 days.

(21) Appl. No.: 12/334,575

(22) Filed: Dec. 15, 2008

(65) Prior Publication Data

US 2009/0155902 A1 Jun. 18, 2009

Related U.S. Application Data

(63) Continuation-in-part of application No. 11/639,566, filed on Dec. 15, 2006, now Pat. No. 7,901,947.

(60) Provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006, provisional application No. 61/013,535, filed on Dec. 13, 2007, provisional application No. 61/091,637, filed on Aug. 25, 2008.

(51) Int. Cl.
| | |
|---|---|
| *C12N 5/00* | (2006.01) |
| *C12P 19/34* | (2006.01) |
| *C12Q 1/68* | (2006.01) |
| *C12Q 1/00* | (2006.01) |
| *G01N 1/10* | (2006.01) |
| *G01N 1/00* | (2006.01) |
| *G01N 35/00* | (2006.01) |

(52) U.S. Cl.
USPC ............ 435/325; 435/6.12; 435/91.2; 435/4; 436/180; 436/43; 436/174

(58) Field of Classification Search
None
See application file for complete search history.

(56) References Cited

U.S. PATENT DOCUMENTS

| | | |
|---|---|---|
| 4,390,403 A | 6/1983 | Batchelder |
| 4,636,785 A | 1/1987 | Le Pesant |
| 4,863,849 A | 9/1989 | Melamede |
| 5,181,016 A | 1/1993 | Lee et al. |
| 5,486,337 A | 1/1996 | Ohkawa |
| 5,770,457 A | 6/1998 | Foote et al. |
| 5,846,396 A | 12/1998 | Zanzucchi et al. |
| 5,851,769 A | 12/1998 | Gray et al. |
| 5,980,719 A | 11/1999 | Cherukuri et al. |
| 6,106,685 A | 8/2000 | McBride et al. |
| 6,130,098 A | 10/2000 | Handique et al. |
| 6,210,891 B1 | 4/2001 | Nyren et al. |
| 6,258,568 B1 | 7/2001 | Nyren |
| 6,294,063 B1 | 9/2001 | Becker et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,473,492 B2 | 10/2002 | Prins |
| 6,485,913 B1 | 11/2002 | Becker et al. |
| 6,538,823 B2 | 3/2003 | Kroupenkine et al. |
| 6,545,815 B2 | 4/2003 | Kroupenkine et al. |
| 6,565,727 B1 | 5/2003 | Shenderov |
| 6,596,238 B1 | 7/2003 | Belder et al. |
| 6,613,560 B1 | 9/2003 | Tso et al. |
| 6,629,826 B2 | 10/2003 | Yoon et al. |
| 6,665,127 B2 | 12/2003 | Bao et al. |
| 6,761,962 B2 | 7/2004 | Bentsen et al. |
| 6,773,566 B2 | 8/2004 | Shenderov |
| 6,790,011 B1 | 9/2004 | Le Pesant et al. |
| 6,828,100 B1 | 12/2004 | Ronaghi |
| 6,838,056 B2 * | 1/2005 | Foster .......................... 422/504 |
| 6,841,128 B2 | 1/2005 | Kambara et al. |
| 6,849,461 B2 * | 2/2005 | Eigen et al. ................... 436/180 |

(Continued)

FOREIGN PATENT DOCUMENTS

| | | |
|---|---|---|
| WO | WO9822625 A1 | 5/1998 |
| WO | WO9915876 A1 | 4/1999 |

(Continued)

OTHER PUBLICATIONS

Yi et al. (2006) Analytica Chimica Acta 560: 1-23.*
Dittrich et al. (2006) Nature Reviews: Drug Discovery 5: 210-218.*
Feng et al. (2004) Chinese Phys Lett. 21, 1851-1854.*
Fu et al. (2002) Anal. Chem. 74, 2451-2457.*
Link et al. (2006) Angew. Chem. Int. Ed. 45, 2556-2560.*
Tourovskaja et al. (2005) Lab. Chip 5, 14-19.*
Zeng et al. (2004) Chin. Phys. Lett. 21(9): pp. 1851-1854.*
Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.
Tuckerman, D.B. and R.F.W. Pease, "High-Performance Heat Sinking for VLSI," IEEE Electron Device Letters, 1981, pp. 126-129.

(Continued)

*Primary Examiner* — Chris R Tate
*Assistant Examiner* — Russell Fiebig
(74) *Attorney, Agent, or Firm* — William A. Barrett; Ward & Smith, P.A.

(57) ABSTRACT

A method of inoculating a culture medium including providing a droplet including a single cell type on a droplet actuator and inoculating a culture medium with the droplet. A method of providing a metabolically useful substance to a cell culture, including providing a droplet actuator including a cell culture droplet loaded thereon, the sample droplet including cells and a cell culture medium, and a second droplet comprising a metabolically useful substance. The method also includes conducting one or more droplet operations to combine the cell culture droplet with the second droplet on the droplet actuator. Related methods, droplet actuators, and systems are also provided.

14 Claims, 9 Drawing Sheets

(56) References Cited

U.S. PATENT DOCUMENTS

| | | |
|---|---|---|
| 6,868,875 B2 | 3/2005 | De Beukeleer et al. |
| 6,896,855 B1 | 5/2005 | Kohler et al. |
| 6,911,132 B2 | 6/2005 | Pamula et al. |
| 6,924,792 B1 | 8/2005 | Jessop |
| 6,949,176 B2 | 9/2005 | Vacca et al. |
| 6,958,132 B2 | 10/2005 | Chiou et al. |
| 6,960,437 B2 | 11/2005 | Enzelberger et al. |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,078,168 B2 | 7/2006 | Sylvan |
| 7,163,612 B2 | 1/2007 | Sterling et al. |
| 7,189,359 B2 | 3/2007 | Yuan et al. |
| 7,189,560 B2 | 3/2007 | Kim et al. |
| 7,211,223 B2 | 5/2007 | Fouillet et al. |
| 7,255,780 B2 | 8/2007 | Shenderov |
| 7,314,567 B2 * | 1/2008 | Wagler et al. ............... 210/656 |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,488,451 B2 | 2/2009 | Sarowitz et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,048,628 B2 | 11/2011 | Pollack et al. |
| 8,075,754 B2 | 12/2011 | Sauter-Starace et al. |
| 8,147,668 B2 | 4/2012 | Pollack et al. |
| 8,221,605 B2 | 7/2012 | Pollack et al. |
| 8,236,156 B2 | 8/2012 | Sarrut et al. |
| 8,287,711 B2 | 10/2012 | Pollack et al. |
| 8,304,253 B2 | 11/2012 | Yi et al. |
| 8,342,207 B2 | 1/2013 | Raccurt et al. |
| 8,349,276 B2 | 1/2013 | Pamula et al. |
| 8,389,297 B2 | 3/2013 | Pamula et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0093651 A1 | 7/2002 | Roe |
| 2002/0125135 A1 | 9/2002 | Derand et al. |
| 2002/0128546 A1 | 9/2002 | Silver |
| 2002/0143437 A1 | 10/2002 | Handique et al. |
| 2002/0168671 A1 | 11/2002 | Burns et al. |
| 2002/0172969 A1 | 11/2002 | Burns et al. |
| 2002/0176804 A1 | 11/2002 | Strand et al. |
| 2003/0006140 A1 | 1/2003 | Vacca et al. |
| 2003/0012483 A1 | 1/2003 | Ticknor et al. |
| 2003/0012699 A1 | 1/2003 | Moore et al. |
| 2003/0015425 A1 | 1/2003 | Bohm et al. |
| 2003/0082081 A1 | 5/2003 | Fouillet et al. |
| 2003/0103021 A1 | 6/2003 | Young et al. |
| 2003/0108452 A1 * | 6/2003 | Fuhr et al. ............... 422/100 |
| 2003/0119057 A1 * | 6/2003 | Gascoyne et al. ............... 435/7.1 |
| 2003/0155034 A1 | 8/2003 | De Beukeleer et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2003/0206351 A1 | 11/2003 | Kroupenkine |
| 2003/0211009 A1 | 11/2003 | Buchanan |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055891 A1 | 3/2004 | Pamula et al. |
| 2004/0058450 A1 | 3/2004 | Pamula et al. |
| 2004/0062685 A1 | 4/2004 | Norton et al. |
| 2004/0091392 A1 | 5/2004 | McBridge et al. |
| 2004/0136876 A1 | 7/2004 | Fouillet et al. |
| 2004/0141884 A1 | 7/2004 | Unno et al. |
| 2004/0231987 A1 | 11/2004 | Sterling et al. |
| 2005/0048581 A1 | 3/2005 | Chiu et al. |
| 2005/0056569 A1 | 3/2005 | Yuan et al. |
| 2005/0064423 A1 | 3/2005 | Higuchi et al. |
| 2005/0084423 A1 | 4/2005 | Zarowitz et al. |
| 2005/0100675 A1 | 5/2005 | Mao et al. |
| 2005/0106742 A1 | 5/2005 | Wahl |
| 2005/0148042 A1 | 7/2005 | Prestwich et al. |
| 2005/0158755 A1 | 7/2005 | Lee et al. |
| 2005/0179746 A1 | 8/2005 | Roux et al. |
| 2005/0227264 A1 | 10/2005 | Nobile et al. |
| 2005/0249636 A1 | 11/2005 | Tacklind et al. |
| 2005/0287572 A1 | 12/2005 | Mathies et al. |
| 2006/0021875 A1 | 2/2006 | Griffith et al. |
| 2006/0054503 A1 * | 3/2006 | Pamula et al. ............... 204/450 |
| 2006/0068450 A1 | 3/2006 | Combette et al. |
| 2006/0164490 A1 | 7/2006 | Kim et al. |
| 2006/0166261 A1 | 7/2006 | Higuchi et al. |
| 2006/0166262 A1 | 7/2006 | Higuchi et al. |
| 2006/0172336 A1 | 8/2006 | Higuchi et al. |
| 2006/0194331 A1 | 8/2006 | Pamula et al. |
| 2006/0231398 A1 | 10/2006 | Sarrut et al. |
| 2006/0254933 A1 | 11/2006 | Adachi et al. |
| 2007/0023292 A1 | 2/2007 | Kim et al. |
| 2007/0025879 A1 | 2/2007 | Vandergaw |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0141593 A1 | 6/2007 | Lee et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0138815 A1 | 6/2008 | Brown et al. |
| 2008/0142376 A1 | 6/2008 | Fouillet et al. |
| 2008/0151240 A1 | 6/2008 | Roth |
| 2008/0153091 A1 | 6/2008 | Brown et al. |
| 2008/0160525 A1 | 7/2008 | Brown et al. |
| 2008/0169184 A1 | 7/2008 | Brown et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171382 A1 | 7/2008 | Brown et al. |
| 2008/0210558 A1 | 9/2008 | Sauter-Starace et al. |
| 2008/0213766 A1 | 9/2008 | Brown et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |

(56) References Cited

U.S. PATENT DOCUMENTS

| | | |
|---|---|---|
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0291433 A1 | 11/2009 | Pollack et al. |
| 2010/0025250 A1 | 2/2010 | Pamula et al. |
| 2010/0048410 A1 | 2/2010 | Shenderov et al. |
| 2010/0126860 A1 | 5/2010 | Srinivasan et al. |
| 2010/0323405 A1 | 12/2010 | Pollack et al. |
| 2012/0165238 A1 | 6/2012 | Pamula et al. |

FOREIGN PATENT DOCUMENTS

| | | | |
|---|---|---|---|
| WO | WO9917093 A1 | 4/1999 | |
| WO | WO9954730 A1 | 10/1999 | |
| WO | 0069565 A1 | 11/2000 | |
| WO | 0073655 A1 | 12/2000 | |
| WO | WO03069380 A1 | 8/2003 | |
| WO | 2004029585 A1 | 4/2004 | |
| WO | 2004030820 | 4/2004 | |
| WO | WO2004027490 A1 | 4/2004 | |
| WO | 2005047696 A1 | 5/2005 | |
| WO | WO2006007701 | * | 1/2006 |
| WO | 2006013303 A1 | 2/2006 | |
| WO | WO2006026351 A1 | 3/2006 | |
| WO | 2006070162 A1 | 7/2006 | |
| WO | 2006081558 | 8/2006 | |
| WO | 2006124458 A2 | 11/2006 | |
| WO | 2006127451 A2 | 11/2006 | |
| WO | 2006134307 A1 | 12/2006 | |
| WO | 2006138543 | 12/2006 | |
| WO | 2007003720 A1 | 1/2007 | |
| WO | 2007012638 A1 | 2/2007 | |
| WO | 2007033990 A1 | 3/2007 | |
| WO | 2007048111 | 4/2007 | |
| WO | 2007120240 A2 | 10/2007 | |
| WO | 2007120241 A2 | 10/2007 | |
| WO | 2007123908 A2 | 11/2007 | |
| WO | WO2007133710 A2 | 11/2007 | |
| WO | 2008051310 A2 | 5/2008 | |
| WO | 2008055256 A3 | 5/2008 | |
| WO | 2008068229 A1 | 6/2008 | |
| WO | 2008091848 A2 | 7/2008 | |
| WO | WO2008091848 A2 | 7/2008 | |
| WO | 2008098236 A2 | 8/2008 | |
| WO | 2008101194 A2 | 8/2008 | |
| WO | 2008106678 A1 | 9/2008 | |
| WO | 2008109664 A1 | 9/2008 | |
| WO | 2008112856 A1 | 9/2008 | |
| WO | 2008116209 A1 | 9/2008 | |
| WO | 2008116221 A1 | 9/2008 | |
| WO | 2008118831 A2 | 10/2008 | |
| WO | 2008124846 A2 | 10/2008 | |
| WO | 2008131420 A2 | 10/2008 | |
| WO | 2008134153 A1 | 11/2008 | |
| WO | 2009002920 A1 | 12/2008 | |
| WO | 2009003184 A1 | 12/2008 | |
| WO | 2009011952 A1 | 1/2009 | |
| WO | 2009021173 A1 | 2/2009 | |
| WO | 2009021233 A2 | 2/2009 | |
| WO | 2009026339 A2 | 2/2009 | |
| WO | 2009029561 A2 | 3/2009 | |
| WO | 2009032863 A2 | 3/2009 | |
| WO | 2009052095 A1 | 4/2009 | |
| WO | 2009052123 A2 | 4/2009 | |
| WO | 2009052321 A2 | 4/2009 | |
| WO | 2009052345 | 4/2009 | |
| WO | 2009052348 A2 | 4/2009 | |
| WO | 2009076414 | 6/2009 | |

OTHER PUBLICATIONS

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Locascio, L.E., et al. "Polymer microfluidic devices," Talanta, vol. 56, Feb. 2002, pp. 267-287.

Garrell, R.L. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May. 2003, pp. 222-228.

Squires, T.M. and S.R. Quake, "Microfluidics: Fluid physics at the nanoliter scale," Reviews of Modern Physics, vol. 77, Oct. 2005, pp. 977-1-26.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y., V.K. Pamula, and K. Chakrabarty, "A Digital-Microfluidic Approach to Chip Cooling," IEEE Design & Test of Computers, vol. 25, Jul. 2008, pp. 372-381.

The, S. -Y., R. Lin, L.-H. Hung, and A.P. Lee, "Droplet microfluidics.," Lab on a chip, vol. 8 Feb. 2008, pp. 198-220.

(56) References Cited

OTHER PUBLICATIONS

I.Barbulovic-Nad, H. Yang, P.S. Park, and A.R. Wheeler, "Digital microfluidics for cell-based assays.," Lab ona chip, vol. 8, Apr. 2008, pp. 519-526.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

R. Sista, Z. Hua, P. Thwar, A Sudarsan, V. Srinivasan, A Eckhardt, M. Pollack, and V. Pamula, "Development of a digital microfluidic platform for point of care testing.," Lab on a chip, vol. 8, Dec. 2008, pp. 2091-2104.

Luk, V.N., Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N. M. Jokerst, and R.B. Fair, "Integrated Optical Sensor in a Digital Microfluidic Platform," IEEE Sensors Journal, vol. 8, May. 2008, pp. 628-635.

R. Mariella, "Sample preparation: the weak link in microfluidics-based biodetection.," Biomedical Microdevices, vol. 10, Dec. 2008, pp. 777-784.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

Jie Ding, "System level architectural optimization of semi-reconfigurable microfluidic system," M.S. Thesis, Duke University Dept of Electrical Engineering, 2000.

Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Moon, Hyejin, Ph.D., "Electrowetting-on-dielectric microfluidics: Modeling, physics, and MALDI application," Ph.D. Dissertation, University of California, Dept. of Mechanical Engineering, Los Angeles, 2006.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Zhang et al., "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.

Fowler, Steve, "Lab-on-a-Chip Technology May Present New ESD Challenges", Electrostatic Discharge (ESD) Journal, Mar. 2002. Retrieved on Apr. 18, 2008 from:http://www.esdjournal.com/articles/labchip/Lab.htm.

Pollack et al, "Electrowetting-Based Actuation of Droplets for Integrated Microfluidics," Lab on a Chip (LOC), vol. 2, pp. 96-101, 2002.

Torkkeli, Alttti, "Droplet microfluidics on a planar surface," Doctoral Dissertation, Department of Electrical Engineering, Helsinki University of Technology (Oct. 3, 2003).

Schwartz. J.A., "Dielectrophoretic Approaches to Sample Preparation and Analysis," The University of Texas, Dissertation, Dec. 2001.

Raj et al., "Composite Dielectrics and Surfactants for Low Voltage Electrowetting Devices," University/Government/Industry Micro/Nano Symposium, vol. 17, pp. 187-190 (Jul. 13-16, 2008).

Kajiyama et al., "Enhancement of Thermostability of Firefly Luciferase from *Luciola lateralis* by a Single Amino Acid Substitution," Biosci. Biotech. Biochem., 58 (6), pp. 1170-1171, 1994.

Jones et al., "Dielectrophoretic liquid actuation and nanodroplet formation," J. Appl. Phys., vol. 89, No. 2, pp. 1441-1448 (Jan. 2001).

Aldrich et al., "PathoFinder: Microscale PCR Based Virus Detection," Yale Department of Engineering Design Course Report, Dec. 2003.

Huang et al., "MEMS-based sample preparation for molecular diagnostics", Analytical and Bioanalytical Chemistry, vol. 372, pp. 49-65 (2002).

Binks, B.P., "Wetting: theory and experiment," Current Opinion in Colloids and Interface Science, vol. 6, No. 1, pp. 17-21, Feb. 2001.

Pollack et al., "Electrowetting-Based Actuation of Droplets for Integrated Microfluidics," Lab on a Chip (LOC), vol. 2, pp. 96-101, 2002.

Al-Rubeai et al., "The effect of Pluronic F-68 on hybridoma cells in continuous culture", Applied Microbiology and Biology 1992, pp. 44-45.

U.S. Appl. No. 12/465,935 Rule 1.132 Declaration Gaurav Jitendra Shah, Jun. 30, 2011.

Furdui et al., "Immunomagnetic T cell capture from blood for PCR analysis using microfluidic systems", Miniaturisation for Chemistry, Biology & Bioengineering, Lab Chip 2004, 4, 614-618.

Liu et al., "Effect of Non-Ionic Surfactants on the Formation of DNA/Emulsion Complexes and Emulsion-Medicated Gene Transfer", Pharmaceutical Research, pp. 1642-1646, vol. 13, No. 11, 1996.

Weber et al., "Specific Blood Purification by Means of Antibody-Conjugated Magnetic Microspheres", Centre for Biomedical Technology, Austria, Scientific and Clinical Applications of Magnetic Carriers, 1997.

Ding, Jie, "System level architectural optimization of semi-reconfigurable microfluidic system," M.S. Thesis, Duke University Dept of Electrical Engineering, 2000.

Fan, Shih-Kang, "Digital Microfluidics by Cross-Reference EWOD Actuation: Principle, Device, and System," PhD Dissertation, University of California Dept. of Mechanical Engineering, 2003.

Moon, Hyejin, Ph.D., "Electrowetting-on-dielectric microfluidics: Modeling, physics, and MALDI application," University of California, Los Angeles, 2006.

Mugele et al., "Electrowetting: from basics to applications," Journal of Physics: Condensed Matter, 17, pp. R705-R774 (Jul. 2005).

Taniguchi et al, "Chemical reactions in microdroplets by electrostatic manipulation of droplets in liquid media," Lab on a Chip, vol. 2, No. 2, pp. 19-23 (2002).

Dewey et al, "Visual modeling and design of microelectromechanical system transducers", Microelectronics Journal, vol. 32, pp. 373-381, Apr. 2001.

Dewey et al, "Towards a visual modeling approach to designing micro electromechanical system transducers," Journal of Micromechanics and Microengineering, vol. 9, pp. 332-340, Dec. 1999.

Fair et al., "Chemical and Biological Applications of Digital Microfluidic Devices", IEEE Design and Test of Computers, vol. 24(1): pp. 10-24 Jan.-Feb. 2007.

Fair et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Fair et al, "Bead-Based and Solution-Based Assays Performed on a Digital Microfluidic Platform," Biomedical Engineering Society (BMES) Fall Meeting, Baltimore, MD, Oct. 1, 2005.

Fair et al, "Electrowetting-based On-Chip Sample Processing for Integrated Microfluidics," IEEE Inter. Electron Devices Meeting (IEDM), pp. 32.5.1-32.5.4, 2003.

Paik et al., "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Paik et al., "Rapid droplet mixers for digital microfluidic systems," Lab on a Chip, vol. 3, pp. 253-259, 2003.

Paik et al "Electrowetting-based droplet mixers for microfluidic systems", Lab on a Chip (LOC), vol. 3, pp. 28-33, 2003.

(56) References Cited

OTHER PUBLICATIONS

Pamula et al., "Cooling of integrated circuits using droplet-based microfluidics," Proc. ACM Great Lakes Symposium on VLSI, pp. 84-87, Apr. 2003.
Pamula et al., "A droplet-based lab-on-a-chip for colorimetric detection of nitroaromatic explosives," Proceedings of Micro Electro Mechanical Systems, pp. 722-725, 2005.
Pollack et al., "Investigation of electrowetting-based microfluidics for real-time PCR applications," μTAS 2003.
Pollack et al., "Electrowetting-Based Microfluidics for High-Throughput Screening," smallTalk2001 Conference Program Abstract (Aug. 2001), p. 149, San Diego.
Ren et al., "Automated electrowetting-based droplet dispensing with good reproducibility," Proc. Micro Total Analysis Systems (mTAS), pp. 993-996, 2003.
Ren et al., "Design and testing of an interpolating mixing architecture for electrowetting-based droplet-on-chip chemical dilution", Transducers 2003, pp. 619-622, 2003.
Srinivasan et al., "An integrated digital microfluidic lab-on-a-chip for clinical diagnostics on human physiological fluids," Lab on a Chip, vol. 4, pp. 310-315, 2004.
Srinivasan et al., "Droplet-based microfluidic lab-on-a-chip for glucose detection," Analytica Chimica Acta, vol. 507, No. 1, pp. 145-150, 2004.
Srinivasan et al., "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.
Srinivasan et al., "Clinical diagnostics on human whole blood, plasma, serum, urine, saliva, sweat, and tears on a digital microfluidic platform," Proc. Micro Total Analysis Systems (mTAS), pp. 1287-1290, 2003.
Srinivasan et al., "A digital microfluidic biosensor for multianalyte detection", Proc. IEEE 16th Micro Electro Mechanical Systems Conference, pp. 327-330, 2003.
Srinivasan et al., "3-D imaging of moving droplets for microfluidics using optical coherence tomography," Proc. Micro Total Analysis Systems (mTAS), pp. 1303-1306, 2003.
Su et al., "Testing of droplet-based microelectrofluidic systems", Proc. IEEE International Test Conference, pp. 1192-1200, 2003.
Weaver, Nicole, "Application of Magnetic Microspheres for Pyrosequencing on a Digital Microfluidic Platform".
PCT International Preliminary Report on Patentability for PCT/US2005/030247 dated Feb. 28, 2007.
PCT International Search Report and Written Opinion for PCT/US2006/047486 dated May 2, 2008.
PCT International Search Report and Written Opinion for PCT/US2006/047481 dated May 5, 2008.
PCT International Search Report and Written Opinion for PCT/US2007/011298 dated Jun. 25, 2008.
PCT International Search Report and Written Opinion for PCT/US2007/009379 dated Aug. 18, 2008.
"Chip mixes droplets faster", MIT Technology Review, Oct. 2003.
"Chip Juggles Droplets", Technology Research News, Sep. 4-11, 2002.
"Laboratory on a Chip", Popular Mechanics, Mar. 2002.
"Lab-on-a-Chip Technology May Present New ESD Challenges", Electrostatic Discharge Journal, Mar. 2002.
"Making materials fit the future: accommodating relentless technological requirements means researchers must recreated and reconfigure materials, frequently challenging established laws of physics, while keeping an eye on Moore's law", R&D Magazine, Dec. 2001.
Srinivasan et al., "Scalable Macromodels for Microelectromechanical Systems", Technical Proc. 2001 Int. Conf. on Modeling and Simulation of Microsystems, pp. 72-75, 2004.
Agah, Ali, "DNA Analysis Chip by Electrowetting Actuation," Stanford Nanofabrication Facility, p. 9, 2002.

Bhansali et al, "Resolving chemical/bio-compatibility issues in microfluidic MEMS systems," SPIE Conference on Microfluidic Devices and Systems II, vol. 3877, Santa Clara, CA, pp. 101-109 (1999).
Cho et al., "Concentration and binary separation of micro particles for droplet-based digital microfluidics," Lab Chip, vol. 7, pp. 490-498, 2007.
Lehmann et al., "Droplet-Based DNA Purification in a Magnetic Lab-on-a-Chip," Angewandte Chemie, vol. 45, pp. 3062-3067, 2006.
Pamme, N., "Magnetism and microfluidics," Lab on a Chip (LOC), vol. 6, pp. 24-38, 2006.
Pipper et al., "Clockwork PCR Including Sample Preparation," Angew. Chem. Int. Ed., vol. 47, pp. 3900-3904, 2008.
Raccurt et al., "On the influence of surfactants in electrowetting systems," J. Micromech. Microeng., vol. 17, pp. 2217-2223 (2007).
Roux et al., "3D droplet displacement in microfluidic systems by electrostatic actuation," Sensors and Actuators A, vol. 134, Issue 2, pp. 486-493, Mar. 15, 2007.
Sista, R., "Development of a Digital Microfluidic Lab-on-a-Chip for Automated Immunoassay with Magnetically Responsive Beads", PhD Thesis, Department of Chemical Engineering, Florida State University, 2007.
Verpoorte, E., "Beads and chips: new recipes for analysis," Lab on a Chip (LOC), vol. 3, pp. 60N-68N, 2003.
Wang et al., "Efficient in-droplet separation of magnetic particles for digital microfluidics," Journal of Micromechanics and Microengineering, vol. 17, pp. 2148-2156 (2007).
Washizu, Masao, "Electrostatic Actuation of Liquid Droplets for Micro-Reactor Applications", IEEE Industry Applications Society Annual Meeting, pp. 1867-1873, Oct. 5-9, 1997.
Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.
Wheeler, Aaron R., "Putting Electrowetting to Work," Science, vol. 322, No. 5901, pp. 539-540, Oct. 24, 2008.
Yi et al., "Geometric surface modification of nozzles for complete transfer of liquid drops," Solid-State Sensor, Actuator and Microsystems Workshop, pp. 164-167, Jun. 6-10, 2004.
Chakrabarty, , "Automated Design of Microfluidics-Based Biochips: connecting Biochemistry of Electronics CAD", IEEE International Conference on Computer Design, San Jose, CA, Oct. 1-4, 2006, 93-100.
Chakrabarty, et al., "Design Automation Challenges for Microfluidics-Based Biochips", DTIP of MEMS & MOEMS, Montreux, Switzerland, Jun. 1-3, 2005.
Chakrabarty, et al., "Design Automation for Microfluidics-Based Biochips", ACM Journal on Engineering Technologies in Computing Systems , 1(3), Oct. 2005, 186-223.
Chakrabarty, K , "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Cotten, et al., "Digital Microfluidics: a novel platform for multiplexed detection of lysosomal storage diseases", Abstract # 3747.9. Pediatric Academic Society Conference, 2008.
Delattre, et al., "Towards an industrial fabrication process for electrowetting chip using standard MEMS Technology", μTAS2008, San Diego; poster presented, Oct. 15, 2008.
Delattre, et al., "Towards an industrial fabrication process for electrowetting chip using standard MEMS Technology", μTAS2008, San Diego; Abstract in proceedings, Oct. 13-16, 2008, 1696-1698.
Fair, et al., "A Micro-Watt Metal-Insulator-Solution-Transport (MIST) Device for Scalable Digital Bio-Microfluidic Systems", IEEE IEDM Technical Digest, 2001, 16.4.1-4.
Fair, , "Biomedical Applications of Electrowetting Systems", 5th International Electrowetting Workshop, Rochester, NY, May 31, 2006.
Fair, et al., "Chemical and biological pathogen detection in a digital microfluidic platform", DARPA Workshop on Microfluidic Analyzers for DoD and National Security Applications, Keystone, CO, 2006.

(56) References Cited

OTHER PUBLICATIONS

Fair, , "Digital microfluidics: is a true lab-on-a-chip possible?", Microfluid Nanofluid, vol. 3, Mar. 8, 2007, 245-281.

Fair, , "Droplet-based microfluidic DNA sequencing", NHGRI PI's meeting, Boston, 2005.

Fair, et al., "Electrowetting-based On-Chip Sample Processing for Integrated Microfluidics", IEEE Inter. Electron Devices Meeting (IEDM), 2003, 32.5.1-32.5.4.

Fair, , "Scaling of Digital Microfluidic Devices for Picoliter Applications", The 6th International Electrowetting Meeting, Aug. 20-22, 2008.

Fouillet, , "Bio-Protocol Integration in Digital Microfluidic Chips", The 6th International Electrowetting Meeting, Aug. 20-22, 2008.

Fouillet, et al., "Digital microfluidic design and optimization of classic and new fluidic functions for lab on a chip systems", Microfluid Nanofluid, vol. 4, 2008 Published On-line Mar. 20, 2007, 159-165.

Hua, et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008,.

Kleinert, et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008. org., Jun. 15-18, 2008.

Marchand, et al., "Organic Synthesis in Soft Wall-Free Microreactors: Real-Time Monitoring of Fluorogenic Reactions", Analytical Chemistry, vol. 80, Jul. 2, 2008, 6051-6055.

Millington, et al., "Digital Microfluidics: a novel platform for multiplexed detection of LSDs with potential for newborn screening", Association of Public Health Laboratories Annual Conference, San Antonio, TX, Nov. 4, 2008.

Paik, et al., "Active cooling techniques for integrated circuits", IEEE Transactions on VLSI, vol. 16, No. 4, 2008, 432-443.

Paik, et al., "Adaptive Cooling of Integrated Circuits Using Digital Microfluidics", accepted for publication in IEEE Transactions on VLSI Systems, 2007, and Artech House, Norwood, MA, 2007.

Paik, , "Adaptive Hot-Spot Cooling of Integrated Circuits Using Digital Microfluidics", Dissertation, Dept. of Electrical and Computer Engineering, Duke University, Apr. 25, 2006, 1-188.

Paik, et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik, et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

Paik, et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik, et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik, et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik, et al., "Programmable flow-through real-time PCR using digital microfluidics", Proc. Micro Total Analysis Systems (µTAS), Handout, 2007.

Paik, et al., "Programmable flow-through real-time PCR using digital microfluidics", Proc. Micro Total Analysis Systems (µTAS), Poster, 2007.

Paik, et al., "Rapid droplet mixers for digital microfluidic systems", Lab on a Chip, vol. 3. (More mixing videos available, along with the article, at LOC's website.), 2003, 253-259.

Pamula, , "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula, et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula, et al., "Digital Microfluidics Platform for Lab-on-a-chip applications", Duke University Annual Post Doctoral Research Day, 2002.

Pamula, et al., "Microfluidic electrowetting-based droplet mixing", IEEE, 2002, 8-10.

Pamula, et al., "Microfluidic electrowetting-based droplet mixing", Proceedings, MEMS Conference Berkeley, Aug. 24-26, 2001, 8-10.

Pamula and Chakrabarty (Co-Chair, , "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.

Pollack, et al., "Electrowetting-based actuation of liquid droplets for microfluidic applications", Appl. Phys. Letters, vol. 77, No. 11, Sep. 11, 2000, 1725-1726.

Pollack, , "Electrowetting-based Microactuation of Droplets for Digital Microfluidics", PhD Thesis, Department of Electrical and Computer Engineering, Duke University, 2001.

Pollack, , "Lab-on-a-chip platform based digital microfluidics", The 6th International Electrowetting Meeting, Aug. 20-22, 2008.

Ren, et al., "Automated on-chip droplet dispensing with volume control by electro-wetting actuation and capacitance metering", Sensors and Actuators B: Chemical, vol. 98, Mar. 2004, 319-327.

Ren, et al., "Dynamics of electro-wetting droplet transport", Sensors and Actuators B (Chemical), vol. B87, No. 1, Nov. 15, 2002, 201-206.

Ren, et al., "Micro/Nano Liter Droplet Formation and Dispensing by Capacitance Metering and Electrowetting Actuation", IEEE-NANO, 2002, 369-372.

Rival, et al., "Towards Single Cells Gene Expression on EWOD Lab on Chip", ESONN 2008, Grenoble, France; Poster presented, Aug. 26, 2008.

Rival, et al., "Towards single cells gene expression on EWOD lab on chip", ESONN, Grenoble, France, abstract in proceedings, Aug. 2008.

Sista, et al., "96-Immunoassay Digital Microfluidic Multiwell Plate", Proc. µTAS, Oct. 12-16, 2008.

Sista, et al., "Development of a digital microfluidic platform for point of care testing", Lab on a chip, vol. 8, Dec. 2008, First published as an Advance Article on the web, Nov. 5, 2008, 2091-2104.

Srinivasan, , "A Digital Microfluidic Lab-on-a-Chip for Clinical Diagnostic Applications", Ph.D. thesis, Dept of Electrical and Computer Engineering, Duke University, 2005.

Srinivasan, et al., "Digital Microfluidic Lab-on-a-Chip for Protein Crystallization", The 82nd ACS Colloid and Surface Science Symposium, 2008.

Srinivasan, et al., "Digital Microfluidics: a novel platform for multiplexed detection of lysosomal storage diseases for newborn screening", AACC Oak Ridge Conference Abstracts, Clinical Chemistry, vol. 54, 2008, 1934.

Srinivasan, et al., "Low cost digital microfluidic platform for protein crystallization", Enabling Technologies for Structural Biology, NIGMS Workshop, Bethesda, MD., Mar. 4-6, 2009, J-23.

Su, et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan, et al., "Printed circuit technology for fabrication of plastic based microfluidic devices", Analytical Chemistry vol. 76, No. 11, Jun. 1, 2004, Previously published on-line, May 2004, 3229-3235.

Wang, et al., "Droplet-based micro oscillating-flow PCR chip", J. Micromechanics and Microengineering, vol. 15, 2005, 1369-1377.

Xu, et al., "A Cross-Referencing-Based Droplet Manipulation Method for High-Throughput and Pin-Constrained Digital Microfluidic Arrays", Proceedings of conference on Design, Automation and Test in Europe (DATE ), Apr. 2007.

(56) References Cited

OTHER PUBLICATIONS

Xu, et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu, et al., "Automated solution preparation on a digital microfluidic lab-on-chip", PSI Bottlenecks Workshop, 2008.

Xu, et al., "Automated, Accurate and Inexpensive Solution-Preparation on a Digital Microfluidic Biochip", Proc. IEEE Biomedical Circuits and Systems Conference (BioCAS), 2008, 301-304.

Xu, et al., "Defect-Aware Synthesis of Droplet-Based Microfluidic Biochips", IEEE, 20th International Conference on VLSI Design, 2007.

Xu, et al., "Design and Optimization of a Digital Microfluidic Biochip for Protein Crystallization", Proc. IEEE/ACM International Conference on Computer-Aided Design (ICCAD), Nov. 2008, 297-301.

XU, et al., "Digital Microfluidic Biochip Design for Protein Crystallization", IEEE-NIH Life Science Systems and Applications Workshop, LISA, Bethesda, MD, Nov. 8-9, 2007, 140-143.

Xu, et al., "Droplet-Trace-Based Array Partitioning and a Pin Assignment Algorithm for the Automated Design of Digital Microfluidic Biochips", CODES, 2006, 112-117.

XU, et al., "Integrated Droplet Routing in the Synthesis of Microfluidic Biochips", IEEE, 2007, 948-953.

Xu, et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu, et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yi, et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi, et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.

Yi, , "Soft Printing of Biofluids for Micro-arrays: Concept, Principle, Fabrication, and Demonstration", Ph.D. dissertation, UCLA, 2004.

Yi, et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi, et al., "Soft Printing of Droplets Pre-Metered by Electrowetting", Sensors and Actuators A: Physical, vol. 114, Jan. 2004, 347-354.

Zeng, et al., "Actuation and Control of Droplets by Using Electrowetting-on-Dielectric", Chin. Phys. Lett., vol. 21(9), 2004, 1851-1854.

Zhang, et al., "Behavioral modeling and performance evaluation of microelectrofluidics-based PCR systems using SystemC", IEEE Transactions on Computer-Aided Design of Integrated Circuits & Systems, vol. 23 (6), Jun. 2, 2004, 843-858.

Zhao, et al., "Droplet Manipulation and Microparticle Sampling on Perforated Microfilter Membranes", J. Micromech. Microeng., vol. 18, 2008, 1-11.

Zhao, et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao, et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao, et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

\* cited by examiner

MANIPULATION OF CELLS ON A DROPLET ACTUATOR

RELATED APPLICATIONS

This continuation-in-part application claims priority to U.S. Patent Application Nos. 61/013,535, entitled "Manipulating cells in a droplet actuator," filed on Dec. 13, 2007; 61/091,637, entitled "Manipulating cells in a droplet actuator," filed on Aug. 25, 2008; and U.S. patent application Ser. No. 11/639,566, entitled "Droplet-based Particle Sorting," filed on Dec. 15, 2006, now U.S. Pat. No. 7,901,947; provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; 60/807,104, entitled "Method and Apparatus for Droplet-Based Nucleic Acid Amplification," filed on Jul. 12, 2006; the entire disclosures of which are incorporated herein by reference.

GRANT INFORMATION

This invention was made with government support under DK066956-02 awarded by the National Institutes of Health of the United States. The United States Government has certain rights in the invention.

FIELD OF THE INVENTION

The inventions relates to methods, devices and systems for sorting cells, inoculating culture media, replenishing culture media, growing cells, and testing cell cultures.

BACKGROUND OF THE INVENTION

Droplet actuators are used to conduct a wide variety of droplet operations, such as droplet transport and droplet dispensing. A droplet actuator typically includes two surfaces separated by a gap. One or both surfaces include electrodes for conducting droplet operations. The gap typically includes one or more filler fluids that are relatively immiscible with the droplets. Droplets may, for example, be reagents and/or droplet fluids for conducting assays. In wide variety of applications, such as the production of antibodies and assaying stem cells, samples within droplet actuators may include cells to be manipulated and, therefore, there is a need for new approaches to manipulating cells within a droplet actuator.

BRIEF DESCRIPTION OF THE INVENTION

The invention provides a method of inoculating a culture medium. The method may include providing a droplet including a single cell type on a droplet actuator and inoculating a culture medium with the droplet. The inoculating step may involve conducting one or more droplet operations to bring the droplet into contact with the culture medium. The droplet including a single cell type may be provided by (a) providing a droplet actuator including a sample droplet loaded thereon, the sample droplet including cells of multiple cell types; (b) dispensing a sub-droplet from the sample droplet; (c) analyzing the sub-droplet to determine whether the sub-droplet includes a single cell type; (d) repeating steps (b) and (c) until one or more droplets each including a single cell or a single cell type is identified.

The invention also provides a method of providing a droplet including a single cell type, the method including: providing a droplet actuator including: a sample droplet loaded thereon, the sample droplet including cells of multiple cell types; a bead droplet including one or more beads having affinity for a specific one of the cell types; conducting one or more droplet operations to combine the bead droplet with the sample droplet, thereby permitting cells of the specific one of the cell types to bind to the beads; conducting a droplet based washing protocol to separate the beads bound to cells of the specific one of the cell types from cells of other cell types.

Further, the invention provides a method of providing a droplet having a modified distribution of cell types, the method including: providing a droplet actuator including a sample droplet loaded thereon, the sample droplet including a first distribution of cells of multiple cell types; activating a series of electrodes to elongate the droplet, thereby providing an elongated droplet; applying a dielectrophoretic gradient along the elongated droplet; deactivating an intermediate one of the series of electrodes to divide the droplet into two or more sub-droplets, each such sub-droplet having a distribution of cells that differs from the first distribution of cells of multiple cell types. At least one of the sub-droplets provided may include a cell type that is enriched relative to the sample droplet. The cell culture droplet and the second droplet may be situated between droplet actuator substrates in proximity to a droplet operations surface. The cell culture droplet may be substantially surrounded by a filler fluid.

In another embodiment, the invention provides a method of providing a metabolically useful substance to a cell culture. A droplet actuator may be provided, including: and a cell culture droplet loaded thereon, the sample droplet including cells and a cell culture medium; a second droplet including a metabolically useful substance. The method may include conducting one or more droplet operations to combine the cell culture droplet with the second droplet on the droplet actuator. The cell culture droplet may be situated between droplet actuator substrates in proximity to a droplet operations surface. The cell culture droplet and the second droplet may be situated between droplet actuator substrates in proximity to a droplet operations surface. The cell culture droplet may be substantially surrounded by a filler fluid. The cell culture droplet and the second droplet may be substantially surrounded by a filler fluid.

The invention provides a method of growing cells on a droplet actuator. The method includes providing a droplet actuator including a cell culture droplet including a cell culture medium and one or more cells; and maintaining the droplet at a temperature suitable for causing the cells to grow in the cell culture medium on the droplet actuator. The cell culture droplet may be situated between droplet actuator substrates in proximity to a droplet operations surface. The cell culture droplet may be surrounded by a filler fluid. The cells may include cells bound to beads.

The invention also provides a method of providing a hybridoma. A droplet actuator may be provided including: a B-cell droplet including a B-cell; and a myeloma cell droplet including a myeloma cell. The method may involve conducting droplet operations to combine the B-cell droplet with the myeloma cell droplet under conditions suitable to cause the fusion of the B-cell with the myeloma cell to produce a hybridoma. The B-cell droplet is situated between droplet actuator substrates in proximity to a droplet operations surface. The myeloma cell droplet is situated between droplet actuator substrates in proximity to a droplet operations surface. The hybridoma may be grown and tested on the droplet actuator. The B-cell droplet may be surrounded by a filler fluid. The myeloma cell droplet may be surrounded by a filler fluid.

In a further embodiment, the invention provides a method of monitoring a cell culture. The method may include providing droplet actuator including a cell culture droplet including a cell culture medium and one or more cells; conducting one or more droplet operations to dispense a sample droplet from the cell culture medium; and testing the sample droplet for one or more target substances. The cell culture droplet may be situated between droplet actuator substrates in proximity to a droplet operations surface. The sample droplet may be dispensed using electrode-mediated droplet operations between droplet actuator substrates in proximity to a droplet operations surface. Testing may be effected using steps including electrode-mediated droplet operations between droplet actuator substrates. The cell culture droplet may be substantially surrounded by a filler fluid. The sample droplet may be substantially surrounded by a filler fluid.

Testing may be effected while the sample droplet is substantially surrounded by a filler fluid. Testing may involve conducting one or more electrode-mediated, droplet-based assays on the droplet actuator. The target substances may include metabolically useful substances.

One or more droplet operations may be used to replace the sample droplet from the cell culture droplet with a replacement droplet added to the cell culture droplet, the replacement droplet including one or more metabolically useful substances. The replacement droplet is dispensed and transported from a droplet actuator reservoir by electrode mediated droplet operations into contact with the cell culture droplet. The replacement droplet may be selected to replace one or more specific substances identified as deficient in the testing step. The testing and replacement of one or more target substances may be automated. The testing may include quantifying one or more metabolic substances.

The invention also provides a method of monitoring a cell culture including: providing cell culture including a cell culture medium and one or more cells and a fluid path to a droplet actuator; providing a cell culture droplet from the cell culture to the droplet actuator via the fluid path; testing the sample droplet for one or more metabolically useful substances. The method may also include replacing one or more metabolically useful substances identified as deficient by the testing step.

Definitions

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated. Examples of other methods of controlling fluid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, and radioactively induced surface-tension gradient); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. Droplet operations may be discrete flow operations, in which each overall operation involves discrete steps, and each discrete step is mediated by the one or more electrodes upon which the droplets reside and/or adjacent electrodes. In certain cases, discrete flow droplet operations may involve movement of droplets through a surrounding filler fluid, as compared to movement of filler fluid to cause droplet movements.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DETAILED DESCRIPTION OF THE INVENTION

The invention provides methods of manipulating cells within a droplet actuator. For example, by use of operations, such as, dispensing droplets from a cell suspension, analyzing the number of droplets in the dispensed droplet, merging the droplet with other droplets containing either specific reagents or other cells, detecting a property of the droplet, and incubating the droplet at a particular temperature. Embodiments of the invention provide a wide variety of techniques, of which the following are examples: (1) sorting droplets by the number of cells in a droplet, (2) sorting droplets by the types of cells in a droplet, (3) merging cell-containing droplets with reagent droplets, (4), incubating cell-containing droplets in order to grow more cells, (5) fusing droplets with different types of cells in a single droplet, (6) separating a single droplet with different types of cells into multiple droplets, each with a reduced number of cell types, (7) growing cells on beads via incubation, (8) culturing cells in a culture reservoir, and (9) performing liquid exchange in a cell-containing culture reservoir.

8.1 Sorting Cell-Containing Droplets

Figure 1:
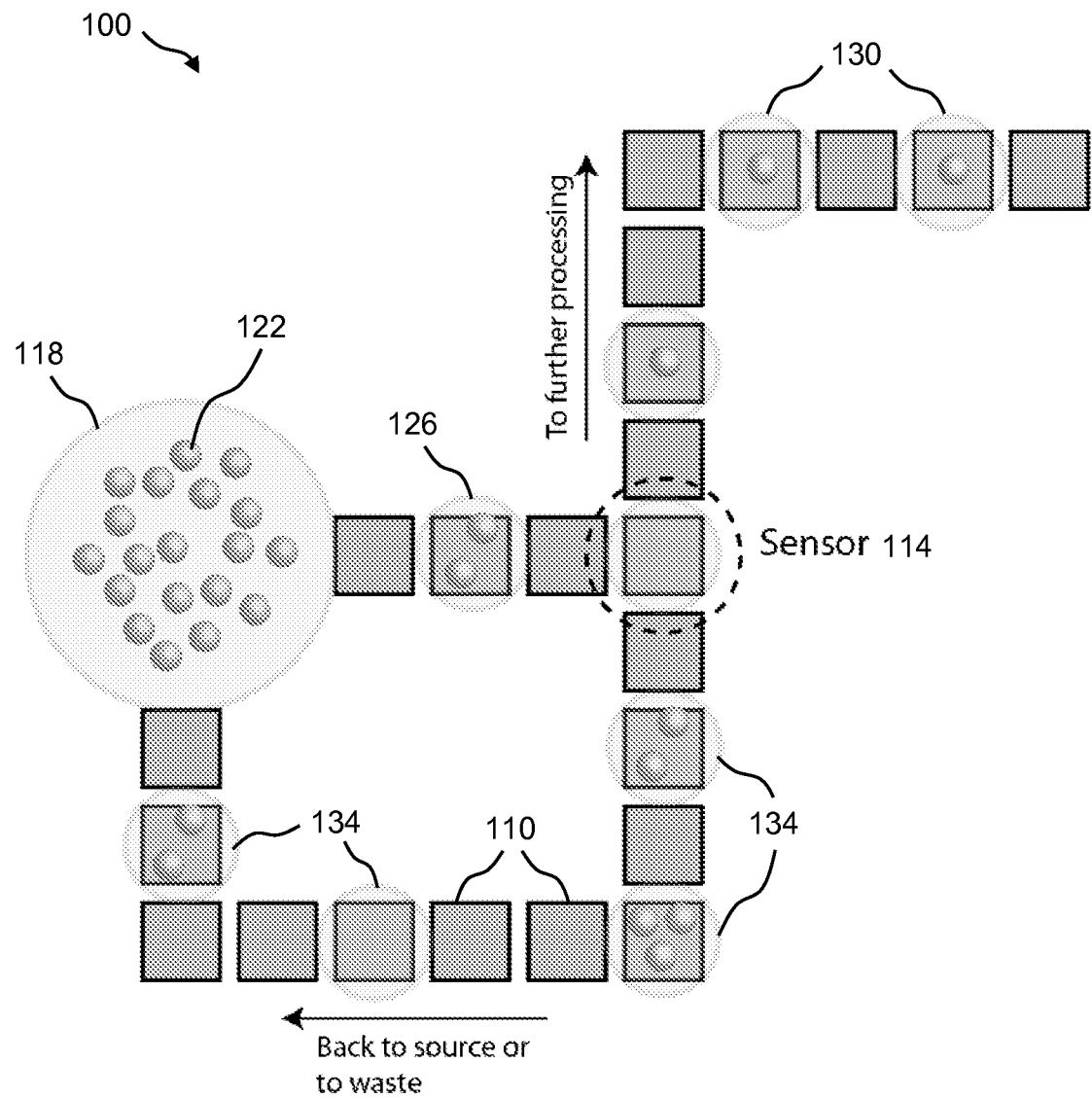
FIG. 1 illustrates a cell sorting process conducted in a droplet actuator.

FIG. 1 illustrates a cell sorting process 100 conducted in a droplet actuator. Droplets are dispensed from a parent droplet or reservoir containing a suspension of cells and dispensed droplets are sorted by the number of cells contained therein. FIG. 1 shows an arrangement of electrodes 110, e.g., electrowetting electrodes, in the droplet actuator. A sensor 114 is provided for detecting the number of cells in a droplet. Sensor 114 may be any suitable detection mechanism for detecting the number of cells in a droplet. Examples include optical detection mechanisms, electrical detection mechanisms, and florescence-based detection mechanisms. Cells may be labeled to facilitate detection. A sample reservoir contains a volume of sample liquid 118 that contains a quantity of cells 122. Droplet operations are used to dispense and transport droplets from the sample, such as a droplet 126. Each dispensed droplet may include a random number of cells. Dispensed droplets are transported along electrodes 110 and into sensing proximity with sensor 114.

In one example scenario, the droplets of interest are those droplets that contain a single cell 122 only and any droplets that contain no cells 122 or two or more cells 122 are discarded or returned to the sample. In this example, when a droplet arrives at sensor 114, the number of cells 122 that are contained therein is determined. In this example, when single-cell droplets, such as single-cell droplets 130, are detected, single-cell droplets 130 are transported along a certain electrode path for further processing. In contrast, when droplets that contain no cells 122 or two or more cells 122, such as droplets 134, are detected, droplets 134 are transported along a certain different electrode path that returns droplets 134 back to the source volume of sample liquid 118 or, alternatively, to a waste reservoir (not shown). The parent droplet may have a concentration of cells selected to statistically (e.g., using Poisson distribution statistics) maximize the number of dispensed droplets including single cells. Droplet operations may be used to dilute excessively concentrated parent droplets in order to improve or maximize the occurrence of dispensed droplets with single cells.

Cell sorting process 100 of sorting droplets by the number of cells is not limited to targeting and processing single-cell droplets only. The target droplets of interest may contain any desired number of cells depending on the intended purpose of the droplet/cell operations within the droplet actuator. For example, two-celled droplets may be targeted and all others are discarded, one- or two-celled droplets may be targeted and all others are discarded, and so on.

Figure 2:
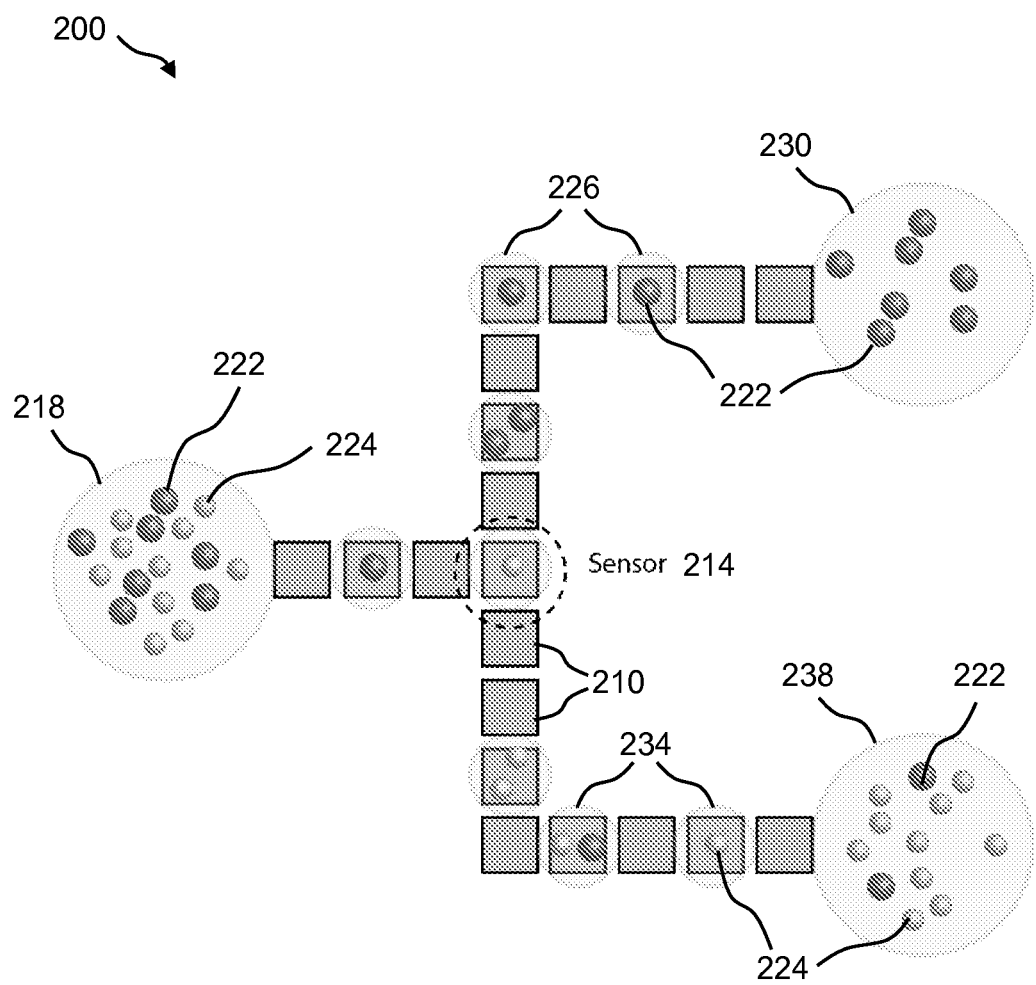
FIG. 2 illustrates a process of sorting droplets in a droplet actuator by the types of cells contained therein.

FIG. 2 illustrates a process 200 of sorting droplets in a droplet actuator by the types of cells contained therein. FIG. 2 shows an arrangement of electrodes 210, e.g., electrowetting electrodes, wherein the location of a sensor 214 is arranged along a transport path for detecting the cell type in a droplet. Sensor 214 may be any suitable detection mechanism for detecting the cell type in a droplet, such as, but not limited to, optical detection mechanisms, electrical detection mechanisms, and florescent-based detection mechanisms. A sample reservoir contains a volume of sample liquid 218 that contains a quantity of various types of cells. In one example, sample liquid 218 contains a quantity of a first cell type 222 and a quantity of a second cell type 224. Droplet operations are used to dispense droplets that contain a random number and cell type and transport the dispensed droplets into proximity with sensor 214.

In one example scenario, the droplets of interest are those droplets that contain the first cell type 222 only and any droplets that contain no cells at all or at least one of the second cell type 224 are discarded. Therefore, when a droplet arrives at sensor 214, the type(s) of cells contained therein is determined. In this example, when droplets that contain one or more of the first cell type 222 only, such as droplets 226, are detected, droplets 226 are transported along a certain electrode path for forming a sample volume 230 that contains the first cell type 222 only. By contrast, when droplets that contain no cells at all or at least one of the second cell type 224, such as droplets 234, are detected, droplets 234 are transported along a different electrode path for forming a waste volume 238 that may contain both the first cell type 222 and the second cell type 224. Alternatively, an electrode path (not shown) may be provided for forming a sample volume that contains the second cell type 224 only.

In another example, the sorting process is used to enrich the concentration of one cell type relative to another cell type. For example, any droplet containing the target cell type may be sorted to one location while any droplet not containing the target cell type may be sorted to a second location. Thus, the first location is enriched with the target cell type while the second location is depleted of the target cell type. This process can be repeated any number of times to achieve a desired level of purification. When the target cell type is labeled, for example, with a fluorescent tag, the sensor may simply need to detect whether or not any signal is present in the droplet to perform this process. For more concentrated cell suspensions the sensor may be used to detect whether the total signal of the droplet exceeds a certain threshold indicating whether the droplet is enriched or depleted of the target cell type. The process can be repeated many times over so that even a relatively small enrichment at each step can produce a substantial amount of purification.

Cell sorting process 200 is not limited to processing two types of cells only. Any number of types of cells may be detected and sorted accordingly into any number of cell type-specific sample volumes. By use of a cell sorting process, such as cell sorting process 200, the invention provides a method of providing droplets with enriched or pure concentrations of pre-selected cell types.

Figure 3A:
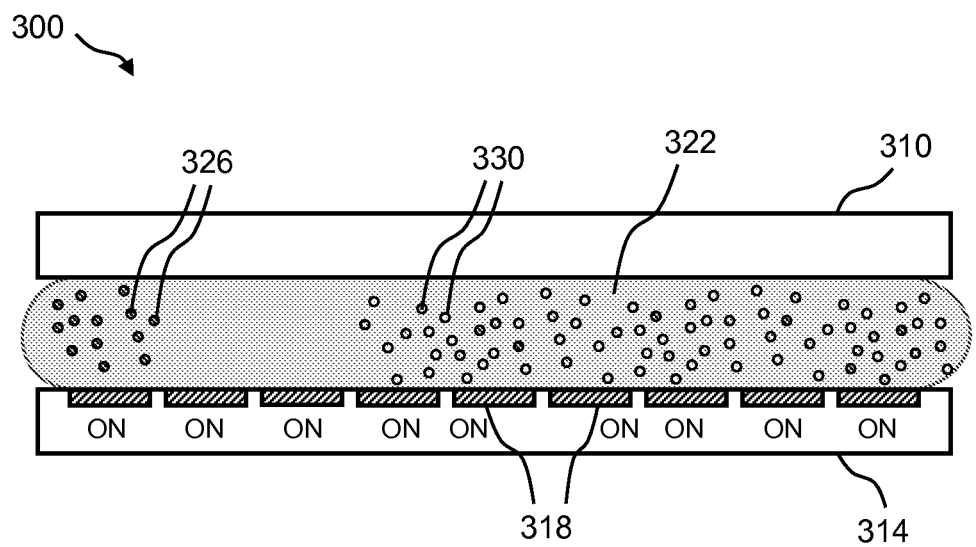
FIGS. 3A and 3B illustrate side views of a first and second step, respectively, of a method of using a droplet actuator for separating different types of cells.
Figure 3B:
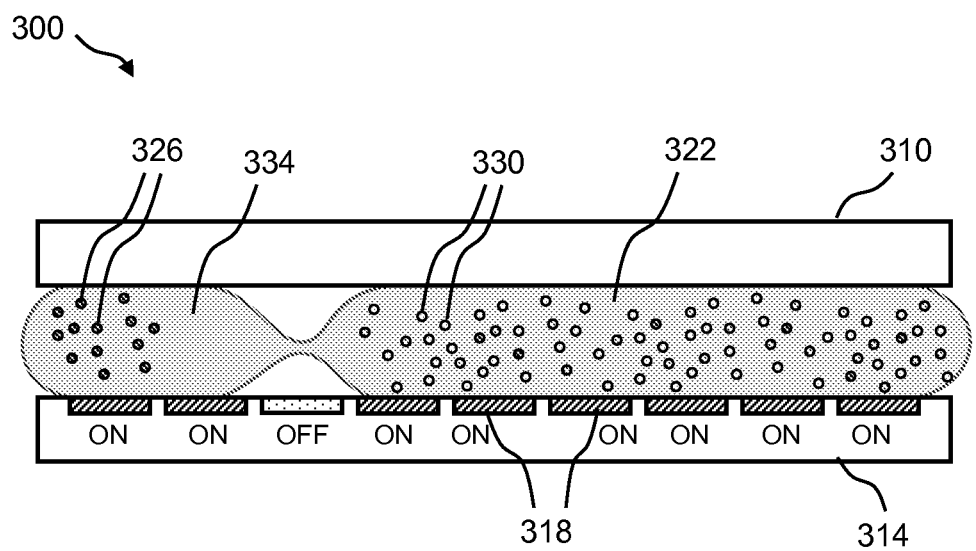

FIGS. 3A and 3B illustrate side views of a first and second step, respectively, of a method of using a droplet actuator 300 for separating different types of cells. Droplet actuator 300 includes a top plate 310 and a bottom plate 314 that are arranged with a gap therebetween. A set of electrodes 318, e.g., electrowetting electrodes, are associated with bottom plate 314. A quantity of sample fluid 322 is provided in the gap of droplet actuator 300. Additionally, sample fluid 322 contains a quantity of cells 326 of interest that are intermixed with a quantity of other types of cells 330. Furthermore, when the dielectric properties of the different types of cells within sample fluid 322 are different, certain electrodes 318 may be used to manipulate certain cells by use of dielectrophoresis (DEP). DEP is the lateral motion imparted on uncharged particles (e.g., cells) as a result of polarization that is induced by non-uniform electric fields (e.g., induced via electrodes 318). For example, FIG. 3A shows a certain electrode 318 that is near one end of the slug of sample fluid 322 is energized in a manner that corresponds to the dielectric properties of the cells 326 of interest. In doing so, the cells 326 of interest are attracted and immobilized (due to DEP) near one end of the slug of sample fluid 322, as shown in FIG. 3A, while the other types of cells 330 that have different dielectric properties are not attracted.

FIG. 3B shows that once the cells 326 of interest are attracted and immobilized (due to DEP) near one end of the slug of sample fluid 322, a droplet splitting operation may occur in order to create a droplet 334 of sample fluid that contains substantially the cells 326 of interest only. By use of the method shown in FIGS. 3A and 3B, cells of interest are separated from unwanted cells via splitting. In another embodiment, DEP may be used to enrich a droplet with cells of interest, and a cell sorting method such as the method described with respect to FIG. 2 may be employed to further isolate a specific cell type.

In an alternative embodiment, different types of beads that have different affinities for different types of cells may be provided within sample fluid 322. In one example, certain beads within sample fluid 322 may have an affinity for the cells 326 of interest and substantially no affinity for the other types of cells 330 and, thus, the cells 326 of interest only bind to these certain beads. Additionally, the beads may have different magnetic properties, for example, by having magnetically responsive beads of different sizes, by providing a mix of magnetically responsive beads and non-magnetically responsive beads, and any combination thereof As a result, a magnetic field strength that corresponds to the beads that have an affinity for the cells 326 of interest may be applied in order to attract and immobilize the target beads near one end of the slug of sample fluid 322. Again, a subsequent droplet splitting operation may occur in order to create a droplet 334 of sample fluid that is enriched for the cells 326 of interest or contains substantially the cells 326 of interest only.

8.2 Merging Droplets Containing Cells

Figure 4:
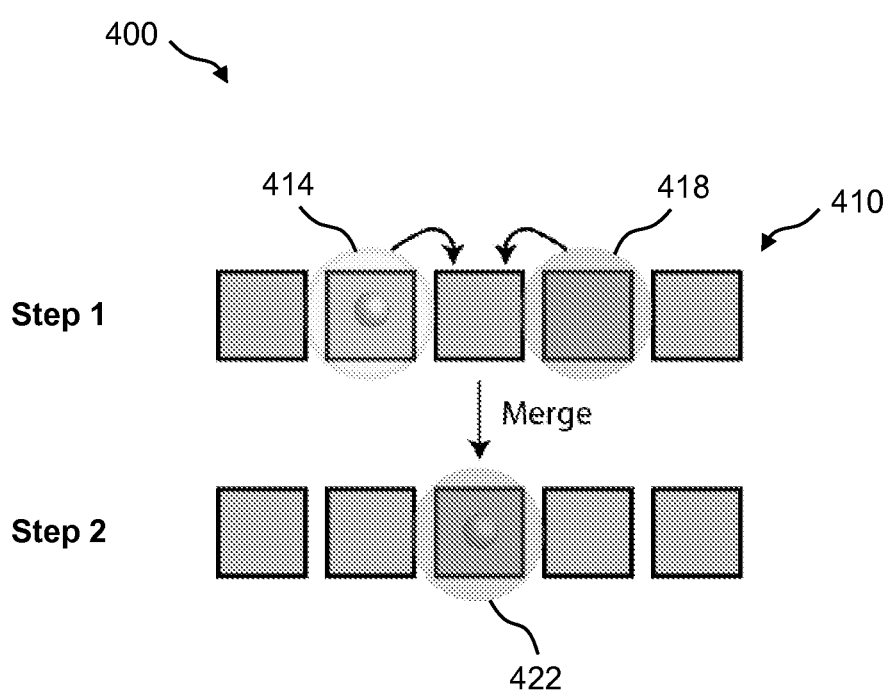
FIG. 4 illustrates a process for merging a droplet containing one or more cells with a droplet of, for example, a reagent.

FIG. 4 illustrates a process 400 for merging a droplet containing one or more cells with a droplet of, for example, a reagent. FIG. 4 shows an arrangement of electrodes 410, e.g., electrowetting electrodes, along which a cell-containing droplet, such as a cell-containing droplet 414, and a droplet of reagent, such as reagent droplet 418, may be manipulated. In particular, a first step of cell merging process 400 shows cell-containing droplet 414 and reagent droplet 418 being transported toward one another along electrodes 410 via electrowetting. A second step of cell merging process 400 shows a merged droplet 422, which is cell-containing droplet 414 and reagent droplet 418 that have been combined into a single droplet. The reagent may, for example, include a nutrient or other reagent for which the cell has a metabolic requirement, a drug or other molecule used to perform a treatment on the cell, such a lysis reagent, or any chemical useful for performing an analysis on the cell.

8.3 Incubating Cells in Droplets

Figure 5:
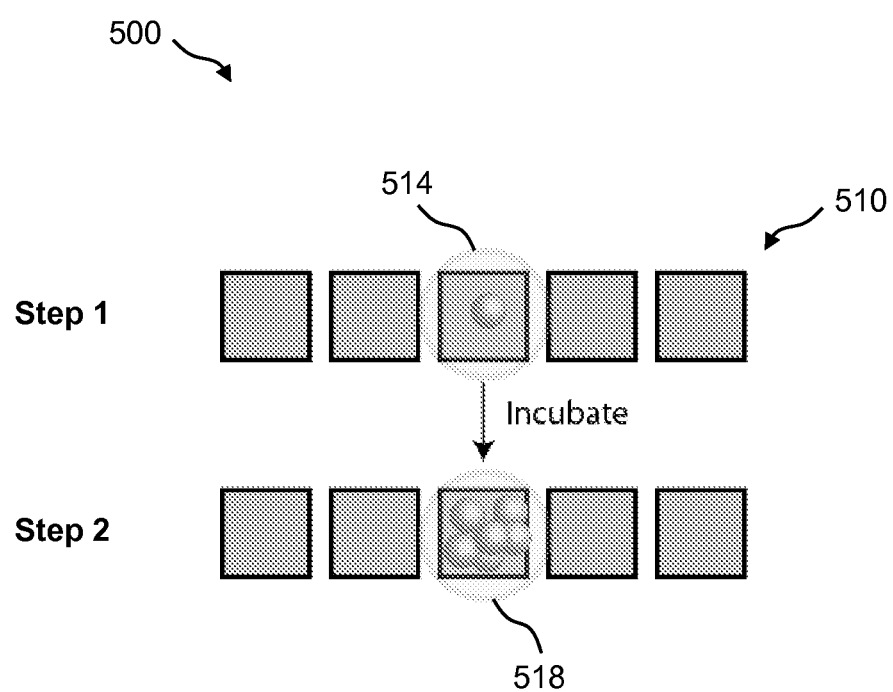
FIG. 5 illustrates a cell incubation process for growing cells in a droplet actuator, e.g., growing cells from a single cell.

FIG. 5 illustrates a cell incubation process 500 for growing cells in a droplet actuator, e.g., growing cells from a single cell. FIG. 5 shows an arrangement of electrodes 510, e.g., electrowetting electrodes, along which a cell-containing droplet, such as a cell-containing droplet 514 may be manipulated. In particular, a first step of cell incubation process 500 shows cell-containing droplet 514 that contains, for example, a single cell only. A second step of cell incubation process 500 is a temperature control step that maintains cell-containing droplet 514 at a temperature that promotes cell growth. The second step shows an incubated droplet 518, which is a droplet that contains multiple cells that have grown over time from the single cell. By use of a cell incubation process, such as cell incubation process 500, cells can proliferate within a droplet actuator. By use of a cell sorting process as described above with respect to FIGS. 1 and 2, and an incubation process, droplets may be obtained having a substantially pure population of cell types.

8.4 Fusing Cells in Droplets

Figure 6:
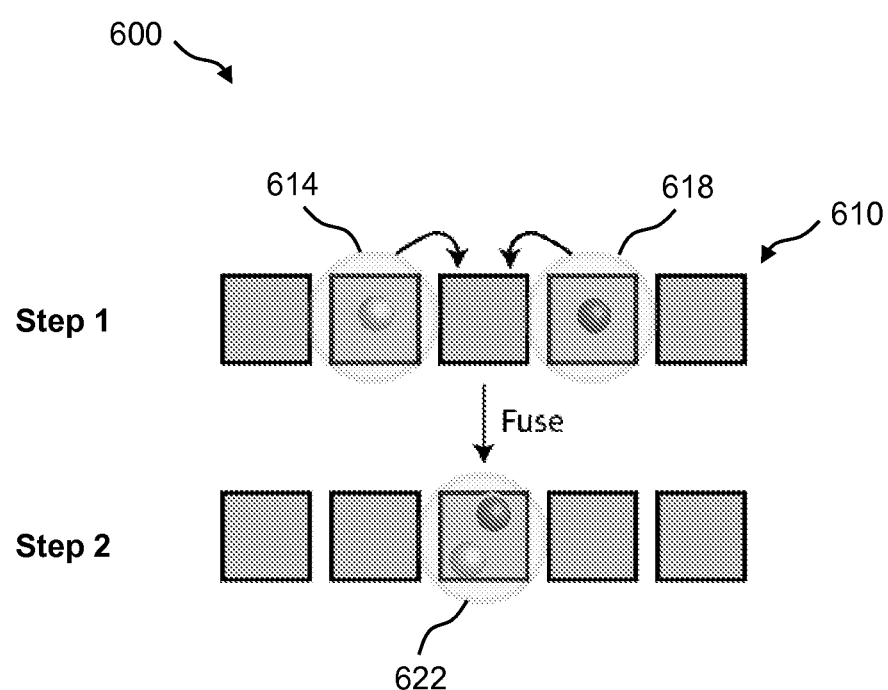
FIG. 6 illustrates a cell fusing process of merging droplets that contain different types of cells.

FIG. 6 illustrates a cell fusing process 600 of merging droplets that contain different types of cells. FIG. 6 shows an arrangement of electrodes 610, e.g., electroweffing electrodes, along which a droplet that contains a first cell type, such as a droplet 614, and a droplet that contains a second cell type, such as droplet 618, may be manipulated. In particular, a first step of cell fusing process 600 shows droplet 614 and droplet 618 being transported toward one another along electrodes 610 via electrowetting. A second step of cell fusing process 600 shows a fused droplet 622, which is droplet 614 and droplet 618 that have been combined into a single droplet that contains both the first and second types of cells, e.g., fusion of a B-cell are with a myeloma cell to produce an antibody-producing hybridoma. In anther example, a fusing process, such as cell fusing process 600, may be used in the in vitro fertilization (IVF) process, i.e., fusing a sperm cell with an egg cell.

8.5 Using Beads for the Manipulation of Cells

Figure 7:
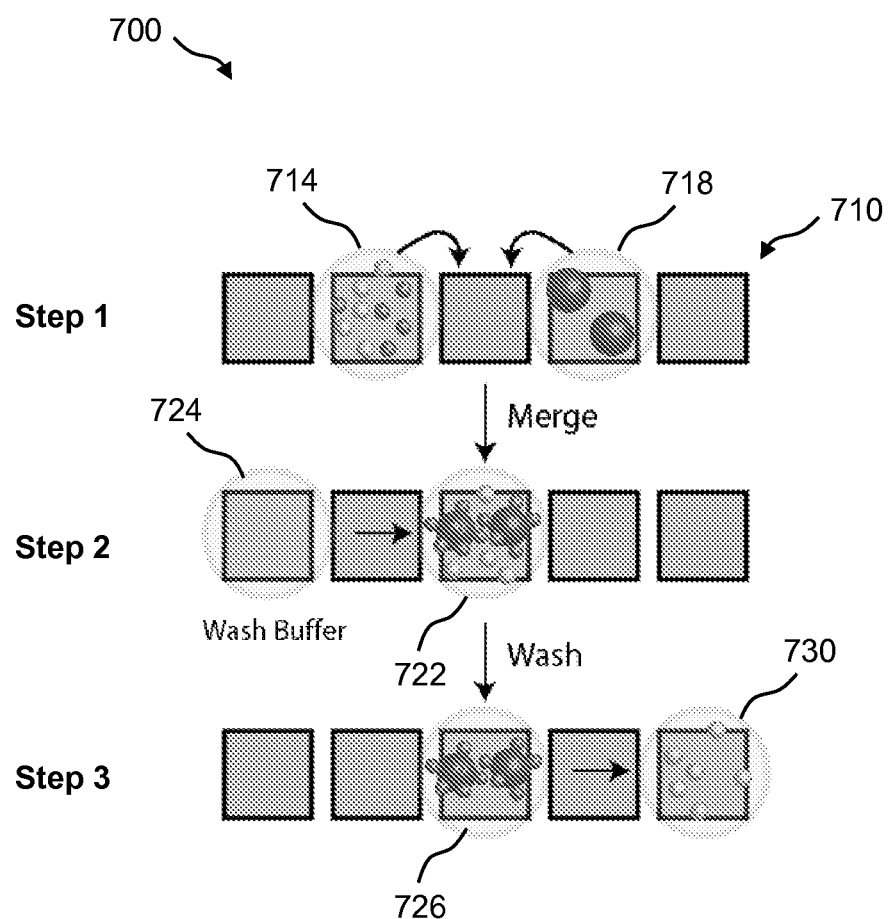
FIG. 7 illustrates a process of separating different cell types by use of beads in a droplet actuator.

FIG. 7 illustrates a process 700 of separating different cell types by use of beads in a droplet actuator. FIG. 7 shows an arrangement of electrodes 710, e.g., electroweffing electrodes, along which a droplet that contains, for example, a first and second cell type, such as a cell-containing droplet 714, and a droplet that contains beads, such as bead-containing droplet 718, may be manipulated. In particular, the beads of bead-containing droplet 718 may be, for example, magnetically responsive beads. Examples of suitable magnetically responsive beads are described in U.S. Patent Publication No. 2005-0260686, entitled, "Multiplex flow assays preferably with magnetic particles as solid phase," published on Nov. 24, 2005. Additionally, the beads of bead-containing droplet 718 may have an affinity for a certain cell type. In one example, the beads of bead-containing droplet 718 may have an affinity for the first cell type only and substantially no affinity for the second cell type.

A first step of cell separation process 700 shows cell-containing droplet 714 and bead-containing droplet 718 being merged along electrodes 710 using electrode-mediated droplet operations. A second step of cell separation process 700 shows a merged droplet 722, which is cell-containing droplet 714 and bead-containing droplet 718 that have been combined into a single droplet that contains both the first and second cell type along with the beads. The second step of cell separation process 700 also shows that the first cell type within merged droplet 722 bind to the beads because the beads have an affinity for the first cell type only. By contrast, cells of the second cell type do not bind to the beads and, thus, remain substantially suspended within merged droplet 722. A third step of cell separation process 700 illustrates a droplet-based wash procedure using wash buffer droplet 724 that is used to remove the unbound second cell type while the beads are restrained in place. The result is a cell-containing droplet 726 that has a substantially pure cell type. The droplet 730 of unbound cells may be subjected to further droplet operations and/or other processing or analysis.

8.6 Growing Cells

Figure 8:
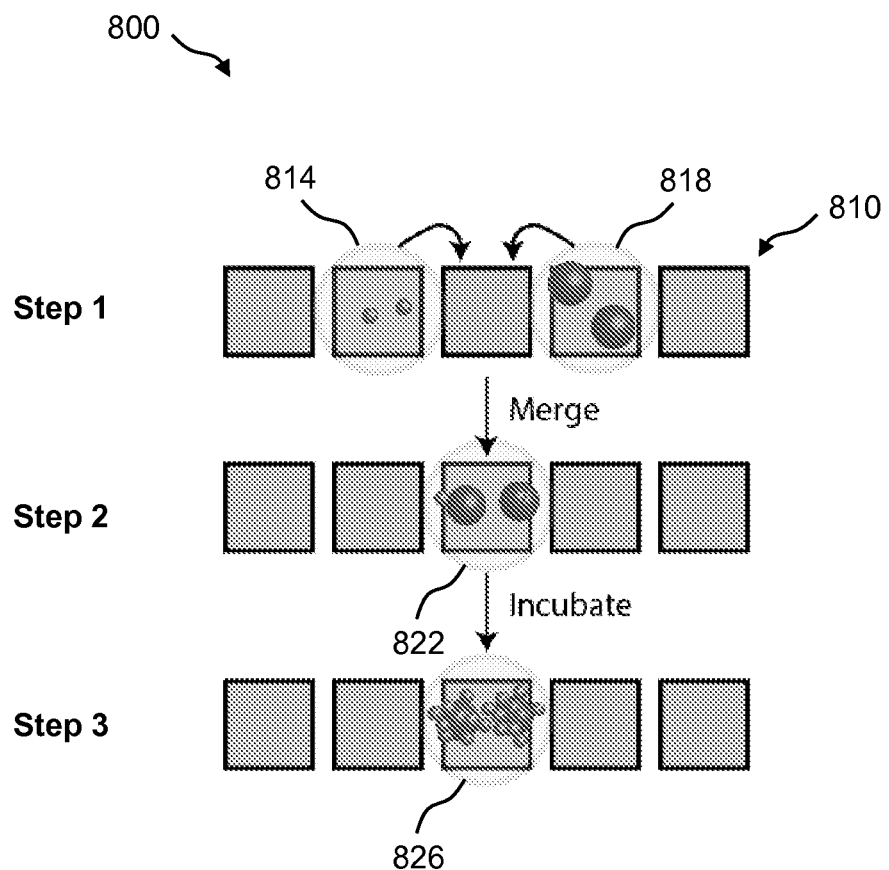
FIG. 8 illustrates a cell incubation process of growing cells on beads in a droplet actuator.

FIG. 8 illustrates a cell incubation process 800 of growing cells on beads in a droplet actuator. FIG. 8 shows an arrangement of electrodes 810, e.g., electrowetting electrodes, along which a droplet that contains a certain cell type, such as a cell-containing droplet 814, and a droplet that contains beads, such as bead-containing droplet 818, may be manipulated. In particular, the beads of bead-containing droplet 818 may be, for example, magnetically responsive beads. Additionally, the beads of bead-containing droplet 818 may have an affinity for the particular cell type within cell-containing droplet 814.

A first step of cell incubation process 800 shows cell-containing droplet 814 and bead-containing droplet 818 being transported toward one another along electrodes 810 via electrowetting. A second step of cell incubation process 800 shows a merged droplet 822, which is cell-containing droplet 814 and bead-containing droplet 818 that have been combined into a single droplet that contains both the cells and the beads. The second step of cell incubation process 800 also shows that the cells within merged droplet 822 bind to the beads because the beads have an affinity for the particular cell type. A third step of cell incubation process 800 is a temperature control step that maintains merged droplet 822 at a temperature that promotes cell growth. The third step of cell incubation process 800 shows an incubated droplet 826, which is a droplet that contains multiple cells that have grown over time upon the surface of the beads. By use of a cell incubation process, such as cell incubation process 800, cells can proliferate within a droplet actuator. In particular, the beads provide a means for growing cells on surfaces other than the droplet actuator surface so that the cells can be subsequently manipulated in the droplet actuator.

Embodiments of the invention may be provided for culturing cells on a droplet actuator. A cell-containing droplet, such as a droplet that contains one or more cells and/or cell-types, may be transported using droplet operations into contact with a cell culture medium. The cell culture medium may be included in a cell culture reservoir or well. When necessary, the cell culture medium may be in contact with the atmosphere or with a sub-atmosphere on the droplet actuator. The droplet actuator may include or be associated with a heating element configured to heat the cell culture medium to an appropriate temperature for incubation.

Figure 9:
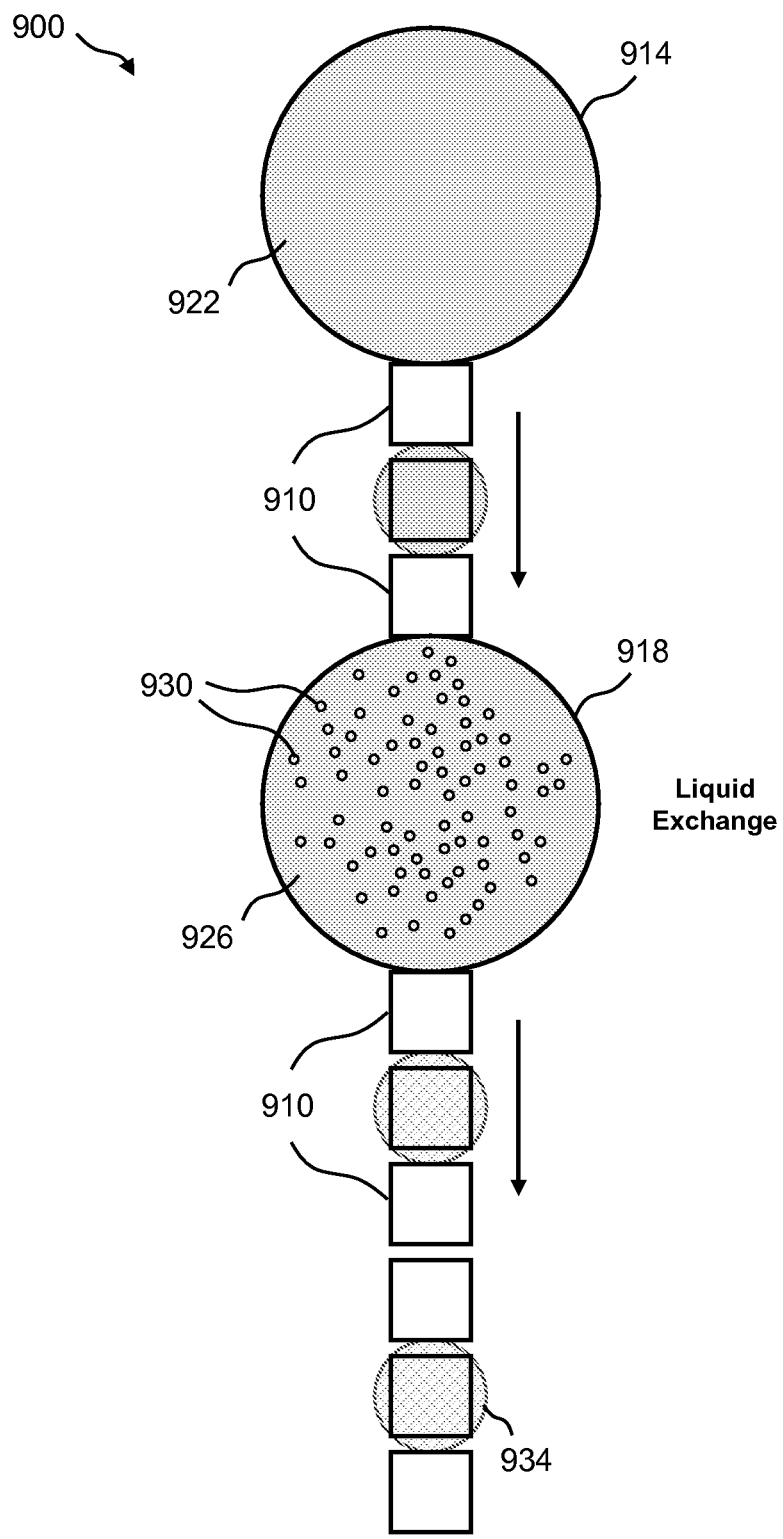
FIG. 9 illustrates a liquid exchange process in a cell culture reservoir.

FIG. 9 illustrates a liquid exchange process 900 in a cell culture reservoir. FIG. 9 shows an arrangement of electrodes 910, e.g., electrowetting electrodes, which fluidically connect a fluid reservoir 914 and a cell culture droplet 918. The arrangement is useful, for example, for performing a liquid exchange process supplying reagents, such as reagents metabolically useful substances, to cell culture droplet 918. Fluid reservoir 914 may contain, for example, a volume of reagent fluid 922. Cell culture droplet 918 may contain, for example, a volume of cell culture medium 926 that contains a quantity of cells 930. Cells 930 may be immobilized within cell culture droplet 918. In one example, cells 930 may be bound to magnetically responsive beads that are within cell culture droplet 918, whereby the magnetically responsive beads may be magnetically immobilized. Similarly, non-magnetically responsive beads may be physically immobilized, e.g., using one or more physical barriers as described in International Patent Application No. PCT/US08/74151, filed on Aug. 25, 2008, entitled "Bead Manipulations on a Droplet Actuator," the entire disclosure of which is incorporated herein by reference. Any mechanism for immobilizing or retaining cells 930 within cell culture droplet 918 is suitable. Liquid may be exchanged using droplet operations for merging nutrient-containing droplets into contact with cell culture droplet 918.

In some cases, droplet splitting operations may also be used to remove droplets including reduced quantities of such nutrients from the cell culture droplet 918.

In one example, by use of droplet operations, droplets of reagent fluid 922 may be dispensed from fluid reservoir 914 and transported along electrodes 910 and into cell culture droplet 918. By introducing reagent fluid 922 into cell culture medium 926 of cell culture droplet 918, reagent fluid 922 is exchanged with cell culture medium 926. Subsequently, one or more droplets 934, which are formed of a mixture of reagent fluid 922 and cell culture medium 926, are transported away from cell culture droplet 918; all the while, cells 930 are held immobilized within cell culture droplet 918. In alternative embodiments, cells 930 are not immobilized.

Example purposes of a liquid exchange process, such as liquid exchange process 900, may include, but are not limited to, delivering in a metered fashion various substances, such as metabolically useful substances, drugs or chemicals, to cell culture medium 926 of cell culture droplet 918, changing the PH concentration of cell culture medium 926 of cell culture droplet 918, changing the concentration of cells 930 within cell culture medium 926 of cell culture droplet 918, and any combinations thereof.

8.7 Inoculation of a Cell Culture Medium

The droplet actuator of the invention may include a cell culture medium arranged in sufficient proximity to one or more droplet operations electrodes to permit a droplet comprising a cell to be introduced to the culture medium. The culture medium itself may be composed on the droplet actuator by combining various droplets including medium components. The culture medium may or may not be subject to droplet operations. In accordance with the invention, a culture medium may be provided on the droplet actuator. A droplet including one or more cells may be transported via droplet operations into contact with the culture medium. The inoculated culture medium may be incubated on the droplet actuator. A droplet may be contacted with a viscous culture medium and removed from the culture medium in order to capture one or more cultured cells, e.g., using the techniques described in International Patent Application No. PCT/US08/74151, filed on Aug. 25, 2008, entitled "Bead Manipulations on a Droplet Actuator," the entire disclosure of which is incorporated herein by reference.

8.8 Testing Cells

Cells on a droplet actuator may be tested using a wide variety of techniques. A cell may be produced on the droplet actuator and tested on the droplet actuator. A cell may be supplied from an external source to the droplet actuator for testing. A reporter assay may be conducted using droplet operations on the droplet actuator to determine whether a gene of interest is being expressed. A RT-PCR assay may be conducted using droplet operations on the droplet actuator using material extracted from the cells using a droplet-based extraction protocol to determine the presence and quantity of mRNA for the gene of interest. An immunoassay may be conducted using droplet operations on the droplet actuator to determine the presence and the amount of protein produced. An enzymatic assay may be conducted using droplet operations on the droplet actuator to determine the activity of the protein. Two or more of these assays or assay types may be conducted on a single droplet actuator.

The results of a combination of the foregoing assays would show the relationship between the expression of the gene, the amount of protein product and the activity of the protein. Cells may be treated with pathogens, therapeutic agents or other test substances or conditions, and the foregoing assays may be conducted to elucidate the effect of the test substance on the cell.

CONCLUDING REMARKS

The foregoing detailed description of embodiments refers to the accompanying drawings, which illustrate specific embodiments of the invention. Other embodiments having different structures and operations do not depart from the scope of the present invention. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of inoculating and maintaining a culture medium, the method comprising:
    (a) providing a droplet actuator comprising a sample droplet loaded thereon, wherein the sample droplet is substantially surrounded by an oil filler fluid and comprises cells of multiple cell types;
    (b) dispensing by electrowetting a sub-droplet from the sample droplet;
    (c) analyzing the sub-droplet to determine whether the sub-droplet comprises a single cell type;
    (d) repeating steps (b) and (c) until one or more sub-droplets each comprising a single cell type is identified; and
    (e) inoculating a culture medium droplet on the droplet actuator by executing electrowetting-mediated droplet operations with a sub-droplet of (c) or (d) comprising a single cell type to bring the sub-droplet into contact with the culture medium droplet to form an inoculated droplet; and
    (f) maintaining the inoculated droplet of (e) at a temperature suitable for causing the cells to grow in the inoculated droplet surrounded by the oil on the droplet actuator, and thereby causing the cells to grow.

2. The method of claim 1 wherein the cells comprise cells bound to beads.

3. The method of claim 1 wherein the cells are labeled.

4. The method of claim 3 wherein the cells are labeled with a labeled antibody.

5. The method of claim 1 further comprising combining the culture medium droplet inoculated with the single cell type with a droplet comprising a substance selected from the group consisting of: beads, particles, microparticles, nanoparticles, drugs, proteins, peptides, antigens, toxins, and antibodies.

6. The method of claim 1 further comprising transporting the culture medium droplet on the droplet actuator.

7. The method of claim 1 wherein the analyzing step comprises conducting an assay comprising droplet-based steps, wherein the assay is mediated by electrowetting electrodes.

8. The method of claim 1 further comprising:
    (a) splitting a dispensed sub-droplet of 1(c) comprising multiple cell type to yield two or more daughter droplets; and
    (b) analyzing one or more of the daughter droplets for the presence of a single particle.

9. The method of claim 1 further comprising:
    (a) combining a dispensed sub-droplet of 1(c) comprising multiple cell type with a buffer droplet;

(b) splitting the dispensed sub-droplet comprising multiple cell type to yield two or more daughter droplets; and
(c) analyzing one or more of the daughter droplets for the presence of a single particle.

10. The method of claim 1 wherein a dispensed sub-droplet of 1(c) lacking cells is transported back to a suspension of cells.

11. The method of claim 1 wherein a dispensed sub-droplet of 1(c) lacking cells is transported into a waste reservoir.

12. The method of claim 1 wherein dispensed sub-droplet sorting decisions are based on a signal detected from the droplet.

13. The method of claim 1 further comprising, after step (f), conducting a droplet based washing protocol to purify the cells of a single cell type.

14. The method of claim 13 wherein the washing protocol comprises a droplet-based merge-and-split protocol.

\* \* \* \* \*